United States Patent
Jervis

(10) Patent No.: US 7,604,609 B2
(45) Date of Patent: Oct. 20, 2009

(54) BENDABLE, REUSABLE MEDICAL INSTRUMENTS WITH IMPROVED FATIGUE LIFE

(75) Inventor: James E. Jervis, Atherton, CA (US)

(73) Assignee: General Surgical Innovations, Inc., North Haven, CT (US)

( * ) Notice: Subject to any disclaimer, the term of this patent is extended or adjusted under 35 U.S.C. 154(b) by 512 days.

(21) Appl. No.: 10/818,044

(22) Filed: Apr. 5, 2004

(65) Prior Publication Data

US 2004/0193104 A1 Sep. 30, 2004

Related U.S. Application Data

(63) Continuation of application No. 09/645,840, filed on Aug. 25, 2000, now abandoned, which is a continuation of application No. 09/026,623, filed on Feb. 20, 1998, now abandoned.

(51) Int. Cl.
*A61M 3/00* (2006.01)
*A61M 1/00* (2006.01)

(52) U.S. Cl. ............................. 604/43; 604/35; 604/44

(58) Field of Classification Search ............... 604/43, 604/281, 95.05, 95.04, 93.01, 129, 173, 531, 604/530, 523, 264, 35
See application file for complete search history.

(56) References Cited

U.S. PATENT DOCUMENTS

| | | | | |
|---|---|---|---|---|
| 4,014,333 A | * | 3/1977 | McIntyre | 604/43 |
| 4,553,957 A | * | 11/1985 | Williams et al. | 604/43 |
| 4,573,979 A | * | 3/1986 | Blake | 604/240 |
| 4,747,820 A | * | 5/1988 | Hornlein et al. | 604/22 |
| 4,889,107 A | | 12/1989 | Kaufman | |
| 4,984,581 A | * | 1/1991 | Stice | 600/585 |
| 5,084,012 A | * | 1/1992 | Kelman | 604/35 |
| 5,217,465 A | * | 6/1993 | Steppe | 606/107 |
| 5,242,449 A | * | 9/1993 | Zaleski | 606/107 |
| 5,308,324 A | * | 5/1994 | Hammerslag et al. | 604/528 |
| 5,328,480 A | * | 7/1994 | Melker et al. | 604/164.11 |
| 5,417,654 A | * | 5/1995 | Kelman | 604/22 |
| 5,514,076 A | | 5/1996 | Ley | |
| 5,514,115 A | | 5/1996 | Frantzen et al. | |
| 5,562,641 A | * | 10/1996 | Flomenblit et al. | 604/531 |
| 5,645,520 A | * | 7/1997 | Nakamura et al. | 600/151 |
| 5,725,552 A | | 3/1998 | Kotula et al. | |
| 5,788,689 A | | 8/1998 | Allan et al. | |

(Continued)

OTHER PUBLICATIONS

*Engineering Aspects of Shape Memory Alloys*, "Ni-Ti-Cu Shape Memory Alloys", W.J. Moberly, K.N. Melton, Butterworth, Heinemann Ltd, 1990, edited by T.W. Duerig, pp. 46, 52-53.

(Continued)

*Primary Examiner*—Nicholas D Lucchesi
*Assistant Examiner*—Victoria P Campbell

(57) ABSTRACT

A needle device which is manufactured from shape memory or pseudo-elastic materials, such as Nickel Titanium alloys, is provided which may be formed and used repeatedly without adverse effects, such as permanent deformation or fatigue failure. The device in accordance with the present disclosure may be provided having an initial shape which a doctor may bend to a desired shape. The device may be easily returned to its initial shape after use by heating the device above a predetermined sterilization temperature. This cycle may be repeated during subsequent uses, substantially extending the life of the instrument, due to the reduced work hardening and enhanced fatigue properties of the Nickel Titanium device.

24 Claims, 3 Drawing Sheets

U.S. PATENT DOCUMENTS

| | | | |
|---|---|---|---|
| 5,846,256 A | | 12/1998 | Mathis et al. |
| 5,871,496 A | | 2/1999 | Ginn et al. |
| 5,957,928 A | * | 9/1999 | Kirwan, Jr. ................. 606/107 |
| 5,997,526 A | * | 12/1999 | Giba et al. .................. 604/531 |
| 6,074,358 A | * | 6/2000 | Andrew et al. ................ 604/28 |
| 6,120,476 A | * | 9/2000 | Fung et al. ............... 604/95.04 |
| 6,281,262 B1 | * | 8/2001 | Shikinami .................... 523/105 |
| 6,319,222 B1 | * | 11/2001 | Andrew et al. ................ 604/28 |
| 6,340,355 B1 | * | 1/2002 | Barrett ........................ 604/27 |
| 6,423,074 B1 | * | 7/2002 | Chen ........................... 606/107 |
| 6,428,503 B1 | * | 8/2002 | Kierce ......................... 604/43 |
| 6,428,553 B1 | * | 8/2002 | Trese ......................... 606/161 |
| 6,432,078 B1 | * | 8/2002 | Peyman ........................ 604/27 |
| 6,447,478 B1 | * | 9/2002 | Maynard ................. 604/95.05 |
| 6,520,955 B2 | * | 2/2003 | Reynard ........................ 606/4 |
| 6,527,736 B1 | * | 3/2003 | Attinger et al. ............... 604/43 |
| 6,561,974 B1 | * | 5/2003 | Grieshaber et al. .......... 600/206 |
| 6,899,694 B2 | * | 5/2005 | Kadziauskas et al. ......... 604/35 |
| 6,932,788 B2 | * | 8/2005 | Kamiyama et al. ............ 604/43 |
| 6,984,230 B2 | * | 1/2006 | Scheller et al. ............... 606/15 |

OTHER PUBLICATIONS

Article entitled "Ni-Ti Based Shape Memory Alloys", K.N. Melton, pp. 21-35, publication unknown.

Article entitled "An Introduction to Martensite and Shape Memory", C.M. Wayman, T.W. Duerig, pp. 3-20, publication unknown.

"Performance Improvement of Surgical Instrumentation Through the Use of Ni-Ti Materials", A. Melzer, C. Stockel, SMST-94: Proceedings of the International Conference on Shape Memory and Superelastic Technology, edited by A.R. Pelton, D. Hodgson, T. Duerig, Mar. 7-10, 1994, pp. 401-409.

"Applications of Superelastic Ni-Ti in Laparoscopy", P.P. Poncet, R. Zadno, SMST-94: Proceedings of the International Conference on Shape Memory and Superelastic Technology, edited by A.R. Pelton, D. Hodgson, T. Duerig, Mar. 7-10, 1994, pp. 421-426.

"Improved NiTi Alloys for Medical Applications", S.M. Russell, D.E. Hodgson, F. Basin, SMST-97: Proceedings of the Second International Conference on Shape Memory and Superelastic Technology, edited by A.R. Pelton, D. Hodgson, S. Russell, T. Duerig, Mar. 2-6, 1997, pp. 429-436.

"Shape Memory Applications in Minimal Access Surgery—The Dundee Experience", T.G. Frank, W. Xu, A. Cuschieri, SMST-97: Proceedings of the Second International Conference on Shape Memory and Superelastic Technology, edited by A.R. Pelton, D. Hodgson, S. Russell, T. Duerig, Mar. 2-6, 1997, pp. 429-436.

"SaphLITE™ Saphenous Vein System", Copyright 1998—Genzyme Surgical Products, May 1998 (4 pages).

* cited by examiner

BENDABLE, REUSABLE MEDICAL INSTRUMENTS WITH IMPROVED FATIGUE LIFE

CROSS-REFERENCE OF RELATED APPLICATIONS

This application is a continuation of application Ser. No. 09/645,840 filed Aug. 25, 2000 now abandoned, which is a continuation of application Ser. No. 09/026,623 filed Feb. 20, 1998 now abandoned, all of which are incorporated herein in their entirety.

FIELD OF THE INVENTION

The present invention relates generally to medical instruments, and more particularly to medical instruments made from alloys, such as Nitinol, which provide repeatably bendable instruments having improved fatigue life.

BACKGROUND OF THE INVENTION

With many medical instruments, it is desirable for a doctor to be able to bend a portion of the instrument, such as the tip, to suit the anatomy of the patient being treated. The instrument may be bent a number of times during a single procedure to adjust the instrument, and/or the instrument may be bent upon completion of a procedure back to its initial shape for reuse, the subsequent procedure typically requiring further bending. When made from conventional metals, such instruments generally work harden when the same general area is subjected to repeated bending. Progressively, elongation may be reduced, and the force required to bend the instrument may be increased. In addition, the work hardening may make it difficult to return the instrument to its original shape, and sometimes after repeated bending, the instrument will fatigue and fail. In metals frequently used for medical devices, such as stainless steel and aluminum, such failure may occur in only a few cycles of severe bending, resulting in devices having limited reusability. This failure occurs because the stress-strain curve for such metals in the plastic range has a positive slope.

Accordingly, there is a need for medical instruments having improved fatigue life and which may be bent for use, or during use, and returned easily to their original shape, thereby providing bendable instruments that may be more effectively reused.

SUMMARY OF THE INVENTION

In accordance with the present invention, medical instruments are manufactured from materials, such as Nitinol alloys, having heat-activated shape memory and/or super-elastic properties with incomplete hysteresis, which provide improved fatigue life. Nitinol alloys, which are exclusively or principally composed of nickel and titanium, exhibit metallurgical properties superior to conventional metals, such as stainless steel and aluminum, in this regard. Martensitic, binary Nitinol, for example, has a stress-strain characteristic which plateaus in a manner permitting unusually large deformations at essentially constant stress through a process of crystallographic twinning. Because of the nature of this twinning, the alloy has comparatively little work hardening which greatly enhances its fatigue properties. Super-elastic Nitinol that does not spontaneously complete its hysteresis cycle after deformation exhibits similar behavior which is due to the formation of stress-induced martensite.

These forms of Nitinol are ideal for the purposes of making instruments which can be formed during repeated use without adverse effects. A bendable instrument in accordance with the present invention may be provided having an initial orientation or shape, a doctor may bend the instrument to a desired shape for use during a procedure, and then the instrument may be returned to its initial shape after use.

For example, a bendable portion of an instrument may be made from a martensitic alloy, that is formed into its initial shape at an elevated temperature while the alloy is in its austenitic phase. During the course of a procedure while at substantially ambient temperatures, the bendable portion may formed into one or more desired shapes. After being used in a procedure, the instrument may be heat sterilized or otherwise heated, thereby automatically returning it to its initial shape such that the user is always presented with a standard shape when the instrument is supplied for subsequent use. This cycle may be repeated during subsequent uses, substantially extending the life of the instrument as compared to conventional instruments, due to the reduced work hardening and enhanced fatigue properties of the Nitinol instrument.

Thus, it is an object of the present invention to provide medical instruments from materials, such as Nitinol alloys, which enhance the fatigue properties of the instruments, allowing the instruments to be repeatably deformed during a series of uses with substantially reduced likelihood of fatigue failure.

Additional objects and features of the present invention will become apparent from consideration of the following description taken in conjunction with the accompanying drawings.

DETAILED DESCRIPTION OF THE PREFERRED EMBODIMENT

Figure 1:
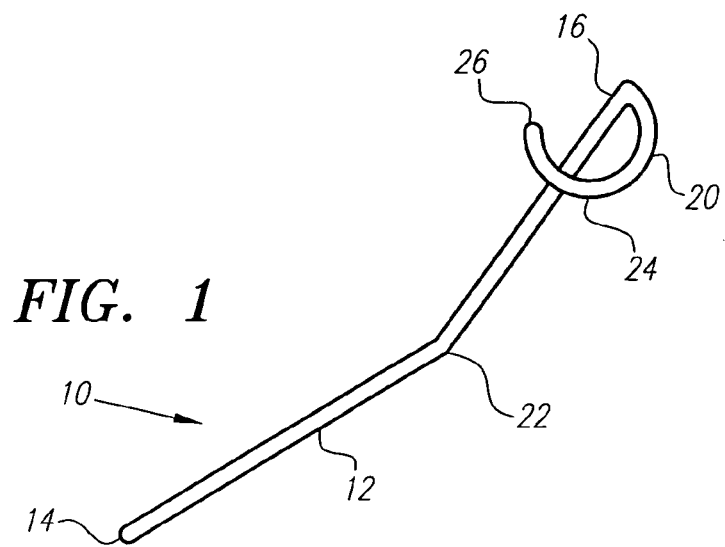
FIG. 1 is a perspective view of a preferred embodiment of a vein harvesting hook in accordance with the present invention.

Generally, medical instruments in accordance with the present invention are manufactured from materials which provide improved bendability and fatigue life. Exemplary materials include those having martensitic transformations, or super-elastic properties without complete hysteresis. Preferred examples comprise alloys of nickel and titanium, possibly including vanadium or copper, i.e., Nitinol alloys.

Shape memory alloys for use in making instruments in accordance with the present invention exhibit a transformation between martensitic and austenitic phases, preferably at temperatures between those experienced when the instruments are used and when the instruments are heat sterilized or otherwise heated before reuse. Such alloys may complete martensitic transformation as they are then cooled and approach temperatures of about 37° C. (i.e. body temperature). Other alloys may remain completely austenitic at temperatures below those used to heat sterilize the instruments, e.g. below approximately 132° C.

To manufacture a reusable bendable instrument in accordance with the present invention, a bendable portion of the instrument may be heated such that the alloy transforms completely to the austenitic phase. The bendable portion may then be formed or constrained in its initial shape at this temperature, i.e., the bendable portion is formed or constrained while the alloy is austenite thereby creating a memory of its initial shape. After being formed, the bendable portion may be cooled, for example to ambient temperatures, and will hold its initial shape. The bendable portion may then be incorporated into the instrument and furnished for use.

During use, a physician, dentist or other user may find it necessary or convenient to form the bendable portion to accommodate the unique anatomy of a patient or to suit various techniques. As the bendable portion is bent, the alloy undergoes crystallographic twinning or phase transformation, rather than undergoing conventional plastic or slip deformation. The bendable portion may be bent repeatedly during the course of a procedure between stable shapes containing twinned martensite, thereby substantially minimizing plastic deformation in the instrument that may accelerate fatigue failure.

After the procedure is complete, the instrument may be heated prior to reuse in a subsequent procedure. As the instrument is heated, the alloy returns to the austenitic phase, and the shape memory property of the alloy causes the bendable portion to revert back into its initial shape.

The instrument may then be cooled once again, and furnished in its initial shape for reuse. Alloys of martensitic Nitinol, for example, are particularly useful for instruments in accordance with the present invention, as they have a deformation characteristic which plateaus in a manner permitting unusually large deformations through this process of crystallographic twinning. Because of the twinning, the alloy has little or no work hardening which greatly enhances its fatigue properties. U.S. Pat. No. 4,505,767 issued to Quin, and T. W. Duerig, Engineering Aspects of Shape Memory Alloys (1990), the disclosures of which are expressly incorporated herein by reference, disclose exemplary alloys suitable for use with instruments in accordance with the present invention. For example, Ni—Ti-5 atomic % Cu which substantially completes martensitic transformation at 56° C., while returning substantially to austenite at 78° C., may provide a satisfactory shape memory alloy for surgical instruments used within the human body (i.e. at temperatures around 37° C.), and heat sterilized for reuse at temperatures of around 132° C. or higher.

Suitable super-elastic Nitinol alloys including atomic percent compositions of Ni, Ti and V, respectively, of 41.5:38.5:20.0, 26.25:33.75:30.0, 47.75:45.75:6.5, 47.5:45.5:7.0, 48.5:46.5:5.0, 45.0:45.0:10.0, 47.5:46.5:6.0, 46.5:46.5:7.0, 48.25:46.25:5.5, and more preferably of 48.0:46.0:6.0, may also be used. These alloys display incomplete superelastic hysteresis and may also exhibit minimal work hardening.

Thus, suitable Nitinol compositions may include atomic percentages of Ni or Ti of at least about 20, more preferably about 30, more preferably about 40 and most preferably about 45. The alloy may or may not include V or Cu, for example having atomic percentages of at least about 1, more preferably about 2, more preferably about 3, more preferably about 4, and most preferably about 5.

These forms of Nitinol are ideal for the purposes of making instruments which can be formed during repeated use without adverse effects. A bendable instrument in accordance with the present invention may be provided having an initial shape or orientation, a doctor may bend the instrument to a desired shape during use, and then the instrument may be easily returned to its initial shape after use without apparent effect. This cycle may be repeated during subsequent uses, substantially extending the life of the instrument compared to conventional instruments, due to the reduced work hardening and enhanced fatigue properties of the Nitinol instrument.

Turning now to the drawings, FIG. 1 shows a preferred embodiment of a medical instrument in accordance with the present invention which is made from a shape memory alloy, such as Nitinol, namely a vein harvesting hook 10 comprising a shaft 12 and a working portion 20. A distal portion 16 of the hook 10 is provided with a standard or initial shape as shown. For example, as shown, the shaft 12 may include a small bend 22 and the working portion 20 may include an arcuate portion 24 that terminates in a distal tip 26. During use in a vein harvesting procedure, a surgeon may bend the hook 10, for example changing the angle of the bend 22, or adjusting the radius of the arcuate portion 24 and the like, perhaps repeatedly, to desired shapes (not shown) suitable for the anatomy encountered during the procedure. After the procedure is completed, the hook 10 may be bent back to its initial shape for reuse, or preferably merely heated, such as during conventional sterilization, to return the hook 10 to its initial shape, as discussed above.

Figure 2:
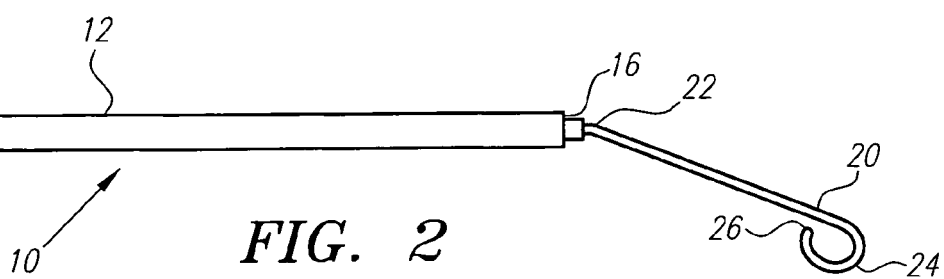
FIG. 2 is a side view of another preferred embodiment of a vein harvesting hook.

FIG. 2 shows another preferred embodiment of a vein harvesting hook 10 in accordance with the present invention. The hook 10 comprises a shaft or handle 12 having a proximal end 14 and a distal end 16, which may be made from conventional metals, such as stainless steel, or plastic. Attached to the distal end 16 is a working portion 20, preferably formed from Nitinol or similar material. As above, the working portion 20 may include a bend 22, an arcuate portion 24, and a distal tip 26, which may be formed during the course of a procedure into one or more desired shapes, and then returned to its initial shape by heating the hook 10 prior to reuse.

Figure 3:
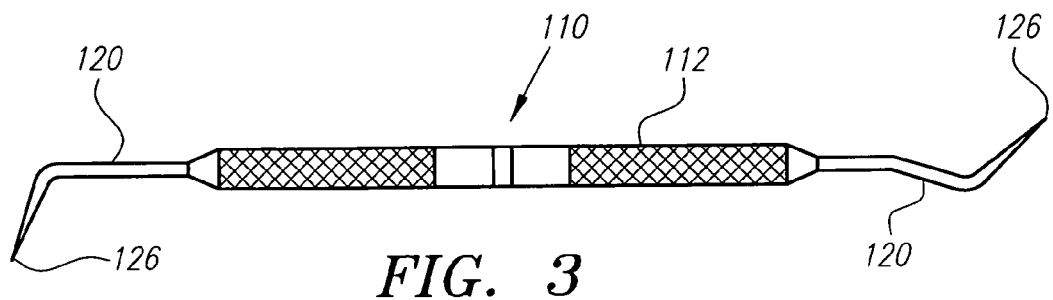
FIG. 3 is a side view of a preferred embodiment of a dental instrument in accordance with the present invention.
Figure 4:
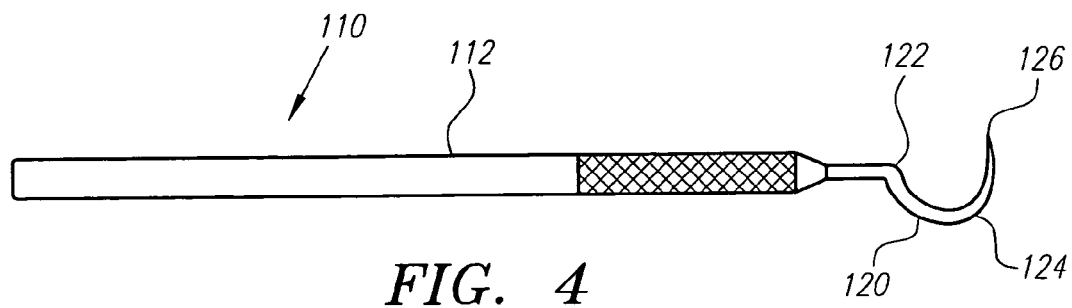
FIG. 4 is a side view of another preferred embodiment of a dental instrument.

FIGS. 3 and 4 show preferred embodiments of a dental instrument 110, which may be provided from shape memory alloys in accordance with the present invention. The instrument 110 includes a shaft 112 formed from conventional materials, having a working portion 120 attached on one end (and optionally both ends as shown in FIG. 3) which is preferably made from Nitinol. During use, a dentist may bend the working portion 120 to accommodate the anatomy of the individual patient or the procedural techniques during the course of treatment. After use, as discussed previously, the instrument 110 may be sterilized, returning the working portion 20 to its initial shape for subsequent reuse. Other dental instruments in accordance with the present invention may include explorers, sealers, scrapers and the like, in which a bendable portion is bent during use and reuse.

Figure 5:
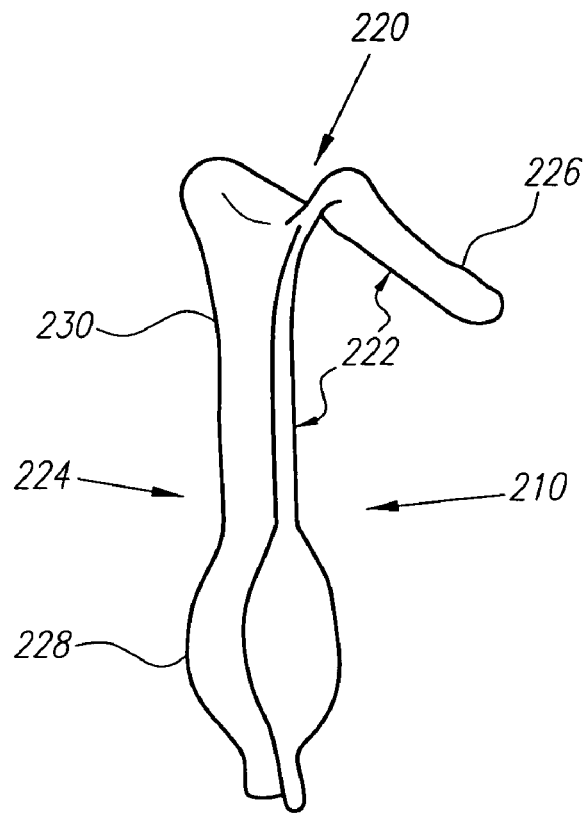
FIG. 5 is a perspective view of a preferred embodiment of a weighted speculum in accordance with the present invention.

Turning to FIG. 5, a weighted speculum 210 in accordance with the present invention is shown. The speculum 210 includes a distal portion 220 and a weighted proximal portion 224, that are formed to have an initial shape, i.e. a predetermined angle 222 between the distal and proximal portions 220, 224. The distal portion 220 has a contoured arm 226 that is adapted to be inserted into the vaginal canal (not shown) to facilitate observation and/or access during a gynecological procedure. The proximal portion 224 includes a weight 228, typically integrally formed in the proximal portion 224, such that when the distal portion 220 is inserted into the vaginal canal, the weight 228 pulls the posterior wall down to maintain an opening for accessing or observing the interior of the vagina.

During a procedure, it may be necessary and/or desirable to change the size of the opening. This is typically achieved by bending the proximal portion 224 in relation to the distal portion 226, i.e. changing the angle 222 therebetween, for example at a location 230 between the arm 226 and the weight 228. This changes the amount of contact that the speculum 220 has with the patient's body, and thereby changes the effective force of the weight 228 on the posterior wall to adjust the size of the opening. After completion of the procedure, the speculum 220 may be heated, for example during sterilization, thereby returning the speculum substantially to its initial shape for reuse.

Figure 6:
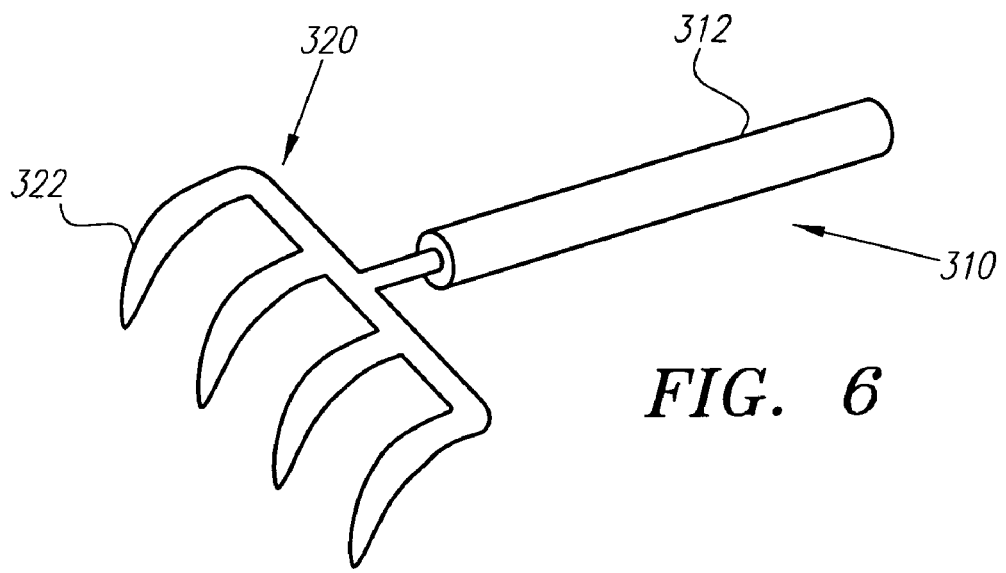
FIG. 6 is a perspective view of a preferred embodiment of a retractor in accordance with the present invention.

Turning to FIG. 6, a "rake"-type retractor 310 in accordance with the present invention is shown, which includes a handle or shaft 312, and a distal portion 320. The distal portion 320 is formed from a shape memory alloy, such as Nitinol, and includes a plurality of tines 322 that have an initial shape, i.e. an initial curvature and/or orientation. During a surgical procedure, the retractor 310 may be used to hold open an incision or other access point into a patient's body (not shown). The tines 322 are typically used to engage tissue and/or bone, and once a desired opening is achieved, the shaft 312 is fixed, for example to a support frame mounted on the surgical table.

Because of the orientation and size of the incision and/or the unique anatomy of the patient, one or more of the tines 320 may be bent to a desired shape to improve contact and/or engagement with the patient's body. After the procedure is complete, the retractor 310 may be heated, thereby returning the tines 320 to their initial shape for reuse in a subsequent procedure.

Figure 7:
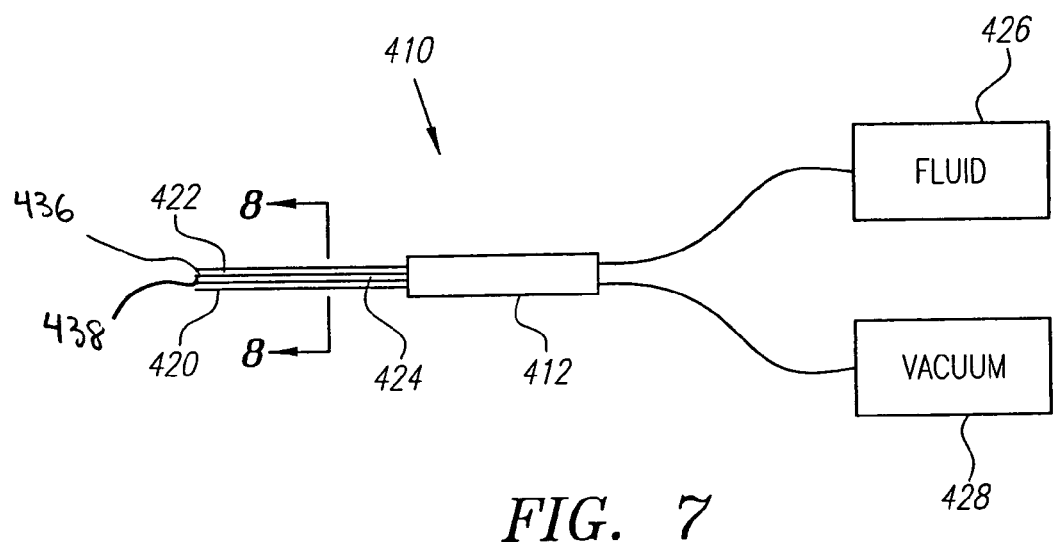
FIG. 7 is a schematic view of a preferred embodiment of a dual lumen needle device in accordance with the present invention.
Figure 8A:
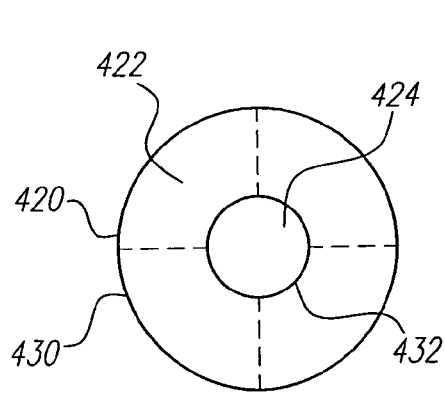
FIGS. 8A and 8B are alternate cross-sectional views of the needle of the dual lumen needle device of FIG. 7, taken along line 8-8.
Figure 8B:
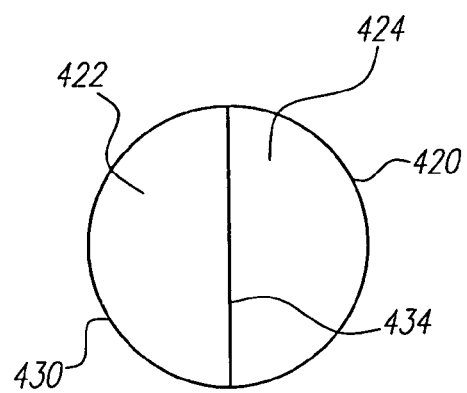

With reference to FIG. 7, a coaxial needle device 410 in accordance with the present invention is shown for use during a cataract surgical procedure. The device 410 includes a conventional handle or shaft 412 and a distal portion 420 that defines a needle that is adapted to be inserted through an incision into a patient's eye. The needle 420 has an irrigation lumen 422 and a vacuum lumen 424 which communicate through the shaft 412 to a source of fluid 428 and a source of vacuum 428, respectively. Irrigation lumen 422 and vacuum lumen 424 have distal ends 436 and 438 that are fixed in relation to one another and disposed or located substantially adjacent to one another, as seen in FIG. 7. The lumens 422 and 424 may be concentric as shown in FIG. 8A, or alternatively, they may be adjacent one another as shown in FIG. 8B.

Generally, the outer cylindrical wall 430 and the interior wall 432 or 434 are formed from a shape memory alloy in accordance with the present invention, preferably Nitinol. Because of the shape memory and/or super-elastic properties of the alloy, the needle 420 may be bent during the course of a procedure, perhaps repeatedly, and then heated upon completion of the procedure to return the needle substantially to its initial shape with minimized risk of fatigue failure during reuse.

For example, the needle device 410 is particularly adapted to be used during a procedure to replace the lens of a cataract patient's eye with an artificial intraocular lens. During such a procedure, an incision is made in the patient's eye to remove the cortical material of the lens. Before an artificial lens is inserted into the eye, the interior of the eye may be repeatedly irrigated and aspirated to ensure that no residual material remains therein. To minimize the number and size of cuts, a dual-lumen needle device is typically used to provide both irrigation and aspiration functions. Preferably, the needle is bent repeatedly during its use to effectively access the entire interior of the eye through a single incision site. Because of the needle's small size and dual lumen construction, however, conventional needle devices are fragile and may break after only a few bends. By comparison, when a needle device 410 in accordance with the present invention is used, the needle 420 may be bent several times during a procedure with minimized risk of failure. Upon completion of the procedure, the needle device 410 may be heated to return the needle 420 substantially to its initial shape for reuse with minimized work hardening and permanent effect on the needle 420.

It will be appreciated by those skilled in the art that the shape memory materials and methods in accordance with the present invention may be used to form a variety of instruments in addition to those specific embodiments described herein, such as retractors, laparoscopic graspers, and the like for which it may be useful to bend a working portion, such as a gripping portion, to accommodate the varying anatomy encountered during individual procedures. The devices may be heated after use, returning the devices substantially to their initial shape for reuse. Thus, an instrument in accordance with the present invention includes both a mechanical component, i.e. bending a portion of the instrument to a desired shape to facilitate its use, and a heat recovery component, i.e. activating the shape memory of the instrument to return it substantially to its initial shape without substantial permanent effect on the instrument. While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A needle device comprising:

a shaft; and a needle extending from one end of the shaft and defining an irrigation lumen and a vacuum lumen, the irrigation lumen being adapted to communicate with a source of irrigation fluid and the vacuum lumen being adapted to communicate with a source of vacuum;

wherein at least a portion of the needle defining the irrigation lumen and the vacuum lumen is formed of a shape memory alloy which is in a martensitic phase at temperatures below about 37° C. and reverts to an austenitic phase at temperatures greater than a predetermined higher sterilization temperature, the needle being capable of retaining a desired bent shape during use after the needle is manually bent in the martensitic phase and reverting to an initial shape when heated to the austenitic phase after use.

2. A needle device according to claim 1, wherein the irrigation lumen and the vacuum lumen are concentric.

3. A needle device according to claim 1, wherein the irrigation lumen and the vacuum lumen are positioned adjacent one another.

4. A needle device according to claim 1, wherein the shaft defines a handle of the device.

5. A needle device according to claim 1, wherein the needle is adapted to be inserted through an incision into a patient's eye.

6. A needle device according to claim 1, wherein the needle includes an outer cylindrical wall and an interior wall, the interior wall separating the irrigation lumen from the vacuum lumen.

7. A needle device according to claim 6, wherein the interior wall is substantially cylindrical.

8. A needle device according to claim 7, wherein the vacuum lumen is defined within the interior wall.

9. A needle device according to claim 8, wherein the irrigation lumen is defined between the outer cylindrical wall and the interior wall.

10. A needle device according to claim 6, wherein the interior wall extends diametrically within the outer cylindrical wall from one side of the outer cylindrical wall to the other side of the outer cylindrical wall.

11. A needle device according to claim 6, wherein both the interior wall and the outer cylindrical wall are formed of a shape memory alloy.

12. A needle device according to claim 11, wherein the shape memory alloy is a nickel titanium alloy.

13. A needle device according to claim 6, wherein at least one of the interior wall and the outer cylindrical wall are formed of a shape memory alloy.

14. A needle device according to claim 13, wherein the shape memory alloy is nickel titanium alloy.

15. A needle device according to claim 1, wherein the shape memory alloy is a nickel titanium alloy.

16. A coaxial needle device according to claim 1 further including a source of fluid and a source of vacuum.

17. A coaxial needle device according to claim 1, wherein the distal end of the irrigation lumen is substantially adjacent the distal end of the vacuum lumen.

18. A coaxial needle device adapted to be inserted through an incision in a patient's eye comprising:
a shaft defining a handle; and
a needle extending from one end of the shaft, the needle defining an irrigation lumen adapted to communicate with a source of irrigation fluid, and a vacuum lumen adapted to be connected to a source of vacuum, the vacuum lumen being positioned within and being concentric with the irrigation lumen;
wherein at least a portion of the needle defining the irrigation lumen and the vacuum lumen is formed of a nickel titanium alloy which is in a martensitic phase at temperatures below about 37° and reverts to an austenitic phase at temperatures greater than a predetermined higher sterilization temperature, the needle being capable of retaining a desired bent shape during use after the needle is manually bent in the martensitic phase and reverting to an initial shape when heated to the austenitic phase after use.

19. A coaxial needle device according to claim 18 further including a source of fluid and a source of vacuum.

20. A coaxial needle device according to claim 18, wherein the distal end of the irrigation lumen is substantially adjacent the distal end of the vacuum lumen.

21. A needle device comprising:
a shaft; and
a needle extending from one end of the shaft and defining an irrigation lumen and a vacuum lumen, the irrigation lumen being adapted to communicate with a source of irrigation fluid and the vacuum lumen being adapted to communicate with a source of vacuum;
wherein the needle is manually bendable from an initial configuration to at least one subsequent configuration, at least a portion of the needle defining the irrigation lumen and the vacuum lumen being at least partially formed from an elastic material maintaining the at least one subsequent configuration during use of the needle and reverting to the initial configuration upon achieving a predetermined temperature after use of the needle, the elastic material being resistant to work hardening to facilitate repeated repositioning of the needle between the initial configuration and the at least one subsequent configuration.

22. A needle device according to claim 21, wherein the elastic material includes a shape memory alloy having a martensitic phase and an austenitic phase.

23. A needle device according to claim 22, wherein the shape memory alloy is in the martensitic phase when the needle is in the initial configuration and the austenitic phase when the needle is in the at least one subsequent configuration.

24. A needle device according to claim 23, wherein the shape memory alloy is in the martensitic phase at temperatures below about 37° C. and the austenitic phase at temperatures greater than the predetermined temperature.

* * * * *

UNITED STATES PATENT AND TRADEMARK OFFICE
CERTIFICATE OF CORRECTION

PATENT NO. : 7,604,609 B2  Page 1 of 1
APPLICATION NO. : 10/818044
DATED : October 20, 2009
INVENTOR(S) : James E. Jervis It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 841 days.

Signed and Sealed this

Fifth Day of October, 2010

David J. Kappos
*Director of the United States Patent and Trademark Office*